US008528545B2

(12) United States Patent
Hodson et al.

(10) Patent No.: US 8,528,545 B2
(45) Date of Patent: Sep. 10, 2013

(54) INHALER DEVICE THAT REDUCES THE RISK FOR MISCOUNTING A DOSAGE (75) Inventors: Darren Hodson, Leicestershire (GB); William Treneman, Cambridgeshire (GB)

(73) Assignee: AstraZeneca AB, Södertäije (SE)

( * ) Notice: Subject to any disclaimer, the term of this patent is extended or adjusted under 35 U.S.C. 154(b) by 1211 days.

(21) Appl. No.: 11/571,645

(22) PCT Filed: Jun. 23, 2005

(86) PCT No.: PCT/SE2005/000996
§ 371 (c)(1), (2), (4) Date: Jan. 4, 2007

(87) PCT Pub. No.: WO2006/004498
PCT Pub. Date: Jan. 12, 2006

(65) Prior Publication Data
US 2008/0060643 A1 Mar. 13, 2008

(30) Foreign Application Priority Data
Jul. 5, 2004 (SE) ........................ 0401786

(51) Int. Cl.
*A61M 11/00* (2006.01)
*A62B 7/00* (2006.01)
*A62B 9/00* (2006.01)

(52) U.S. Cl.
USPC ................. 128/200.23; 128/205.23

(58) Field of Classification Search
USPC ............. 128/200.14, 200.19, 202.22, 203.23, 128/200.23, 205.23; 604/97.03
See application file for complete search history.

(56) References Cited

U.S. PATENT DOCUMENTS

| 3,565,070 | A | * | 2/1971 | Hanson et al. | ........... 128/200.23 |
| 3,900,138 | A | * | 8/1975 | Phillips | ........................ 222/340 |
| 4,817,822 | A | | 4/1989 | Rand et al. | |
| 5,411,173 | A | | 5/1995 | Weinstein | |
| 5,482,030 | A | | 1/1996 | Klein | |
| 5,505,192 | A | | 4/1996 | Marx | |
| 5,718,355 | A | | 2/1998 | Garby et al. | |
| 5,724,957 | A | | 3/1998 | Rubsamen et al. | |
| 5,871,007 | A | * | 2/1999 | Clark, Jr. | ................. 128/200.23 |

(Continued)

FOREIGN PATENT DOCUMENTS
EP 0381494 8/1990
EP 0684047 11/1995
(Continued)

*Primary Examiner* — Kristen Matter
(74) *Attorney, Agent, or Firm* — Finnegan, Henderson, Farabow, Garrett & Dunner, LLP (57) ABSTRACT

Inhaler device (10) comprising an actuator body (20) and an inhaler canister assembly (70), the inhaler canister assembly (70) is comprised of a canister (30) with a metering valve at a valve end and a dose counter unit (60) attached to a base end thereof. Further, the inhaler canister assembly (70) comprises first position ensuring means (110, 230), the actuator body comprises second position ensuring means (120,210), wherein the first and second position ensuring means being complementary mating means, and the first and second position ensuring means being so arranged that the inhaler device (10) cannot be fired, nor the counter unit (60) count unless the first and second position ensuring means are in a mating relationship. There is also provided an inhaler canister assembly (70) and an actuator body (20).

31 Claims, 6 Drawing Sheets

(56) References Cited

U.S. PATENT DOCUMENTS

| | | | |
|---|---|---|---|
| 5,904,139 A * | 5/1999 | Hauser | 128/200.23 |
| 6,082,358 A | 7/2000 | Scarrott et al. | |
| 6,435,372 B1 | 8/2002 | Blacker et al. | |
| 6,446,627 B1 | 9/2002 | Bowman et al. | |
| 6,901,929 B2 | 6/2005 | Burr et al. | |
| 6,953,039 B2 | 10/2005 | Scarrott et al. | |
| 6,971,381 B2 | 12/2005 | Langford | |
| 7,191,918 B2 * | 3/2007 | Ouyang et al. | 222/36 |
| 7,308,893 B2 | 12/2007 | Boot | |
| 7,464,708 B2 * | 12/2008 | Marx | 128/205.23 |
| 2002/0153005 A1 | 10/2002 | Scarrott et al. | |
| 2002/0189611 A1 | 12/2002 | Greenwood et al. | |
| 2003/0188741 A1 | 10/2003 | Scarrott et al. | |
| 2004/0149773 A1 * | 8/2004 | Ouyang et al. | 222/36 |
| 2004/0211420 A1 | 10/2004 | Minshull et al. | |
| 2004/0221840 A1 * | 11/2004 | Stockman-Lamb | 128/200.23 |
| 2004/0255935 A1 | 12/2004 | Bruna | |
| 2005/0284471 A1 * | 12/2005 | Bruna | 128/200.23 |
| 2006/0018991 A1 | 1/2006 | Hoogland | |
| 2007/0079828 A1 * | 4/2007 | Boot | 128/200.23 |
| 2008/0066742 A1 | 3/2008 | Hodson et al. | |
| 2008/0083408 A1 | 4/2008 | Hodson et al. | |

FOREIGN PATENT DOCUMENTS

| | | |
|---|---|---|
| EP | 0 826 386 B1 | 11/2003 |
| EP | 1369139 | 12/2003 |
| GB | 2 191 032 A | 12/1987 |
| GB | 2288259 | 10/1995 |
| GB | 2 360 272 A | 9/2001 |
| JP | 10-267700 A | 10/1998 |
| WO | WO 86/02275 | 4/1986 |
| WO | WO 96/03172 | 2/1996 |
| WO | WO 96/16686 | 6/1996 |
| WO | WO 98/56444 | 12/1998 |
| WO | WO 99/57019 A2 | 11/1999 |
| WO | WO 01/28887 | 4/2001 |
| WO | WO 01/37909 | 5/2001 |
| WO | WO 02/067844 | 9/2002 |
| WO | WO 03/101514 | 12/2003 |
| WO | WO 03/101514 A1 | 12/2003 |
| WO | WO 2004/001664 | 12/2003 |
| WO | WO 2004/041334 A2 | 5/2004 |
| WO | WO 2004/089451 | 10/2004 |
| WO | WO 2006/004496 | 1/2006 |
| WO | WO 2006/004496 A1 | 1/2006 |
| WO | WO 2006/004497 | 1/2006 |
| WO | WO 2006/004498 | 1/2006 |

* cited by examiner

INHALER DEVICE THAT REDUCES THE RISK FOR MISCOUNTING A DOSAGE

CROSS-REFERENCE TO RELATED APPLICATIONS

This application is a national phase application under 35 U.S.C. §371 of PCT International Application No. PCT/SE2005/000996, filed Jun. 23, 2005, which claims priority to Swedish Application Serial No. 0401786-9, filed Jul. 5, 2004.

The present invention relates to the art of inhaler devices, and in particular to an inhaler device that ensures that a canister assembly is correctly inserted into an actuator body.

BACKGROUND OF THE INVENTION

Many types of medicines are provided in fluid form, such as a solution or suspension of particles in a propellant or emulsion, and are adapted for oral inhalation by a patient. As one example, a canister might contain asthma medicine such as fluticasone propionate.

Inhaler devices are commonly used for delivery of a wide range of medicaments. Such an inhaler device normally comprises an actuator body that holds a canister of medicament, the canister being actuated by compression to deliver a dose of medicament through a mouthpiece to a user.

Canisters for holding a suspension or solution of a pharmaceutical substance in a propellant under pressure are well known. One such known canister to be used in an inhalation device comprises a can coupled with a metering valve. The metering valve consists of a body comprising a chamber, a valve stem (which extends from a head of the body) and a metering chamber, selectively communicable by the valve stem to the atmosphere via an L-shaped conduit within the valve body. The valve stem is axially displaceable between a first, extended position in which the metering chamber, and hence the canister, is closed to the atmosphere (since the L-shaped conduit is disposed wholly outside the metering chamber), and a second, depressed position, in which the metering chamber is in open communication with the outlet provided by the L-shaped conduit in the valve stem and through which a metered dose of propellant containing pharmaceutical substance is delivered. Inserted in the inhaler device, the valve stem is inserted into a stem receiving body, which is part of the actuator body. The patient presses down on the base of the canister, held in an inverted position in the actuator body, whereby the valve stem is forced against the stem receiving body in the inside of the actuator, and when the valve stem has been depressed sufficiently to open the metering channel, the inhaler will discharge a single dose. This is known as the firing of the inhaler device. This technology is well known and described in many parts of the prior art. For example in Respiratory Drug delivery, Ed Peter Byron, CRC press, 1991, and in Lung Biology in Health and Disease, Vol 94, Inhalation Aerosols, A J Hickey, Publisher Marcel Decker, 1996 and in Pharmaceutical Preformulation and Formulation, Ed Mark Gibson, Chapter 10, Inhalation Dosage Forms, IHS Health Group, 2001.

It is important for the patient to be able to ascertain the level of medicament remaining in the canister. This requirement is met by the use of a dose counter unit either attached to or part of the inhaler device. It is obvious that this counter must be accurate in that over-counting results in medicament being left in the inhaler unnecessarily resulting in more repeat prescribing with their resultant costs and inconvenience to patient. It also means that in an emergency situation the patient may not use the inhaler in the belief that it is empty when it is not. Conversely, undercounting could result in the inhaler being empty of medicament before the patient has a replacement, which could be dangerous for the patient and reduce patient compliance. Regulatory guidelines require the over and undercounting errors to be minimised.

An inhaler traditionally contains from 120 to 200 doses (shots) so any counter must be reliable, accurate and easy to read. There are many examples of dose counters in the prior art, some located near the valve region of the canister and some attached to the base end of the canister which due to the fact that the canister is in an inverted position in the inhaler mouthpiece means that the counter is on the top of the assembled inhaler and can be easily viewed.

In U.S. Pat. No. 4,817,822 a counter attached to the base end of the canister forming an inhaler canister assembly, is disclosed. A problem with the counter disclosed in U.S. Pat. No. 4,817,822 is that the counter actuation member is arranged in a non protected position, whereby it can be actuated by mistake or tampered with. Moreover, the inhaler canister assembly can be placed in the wrong orientation in the actuator body, whereby the inhaler device could be fired without actuating the counter.

In WO 02/067844 a counter attached to the base of the canister is disclosed where the counter actuator means extends along the whole periphery of the top edge of the actuator body. One problem with this design is that the counter actuation member could easily be tampered with. Moreover counters attached to canisters containing different medicament could easily be interchanged between different actuators and made to operate

SUMMARY OF THE INVENTION

The object of the invention is to provide a new inhaler device, inhaler canister assembly and actuator body, which overcome one or more drawbacks of the prior art. This is achieved by the inhaler device as defined in claim 1, the inhaler canister assembly as defined in claim 10 and the actuator body as defined in claim 11.

One advantage with such a device is that there is a greatly reduced risk for miscounting when firing the device or tampering with the counter.

Embodiments of the invention are defined in the dependent claims.

BRIEF DESCRIPTION OF THE DRAWINGS

The invention will be described in detail below with reference to the drawings, in which.

DETAILED DESCRIPTION OF PREFERRED EMBODIMENTS

Figure 1:
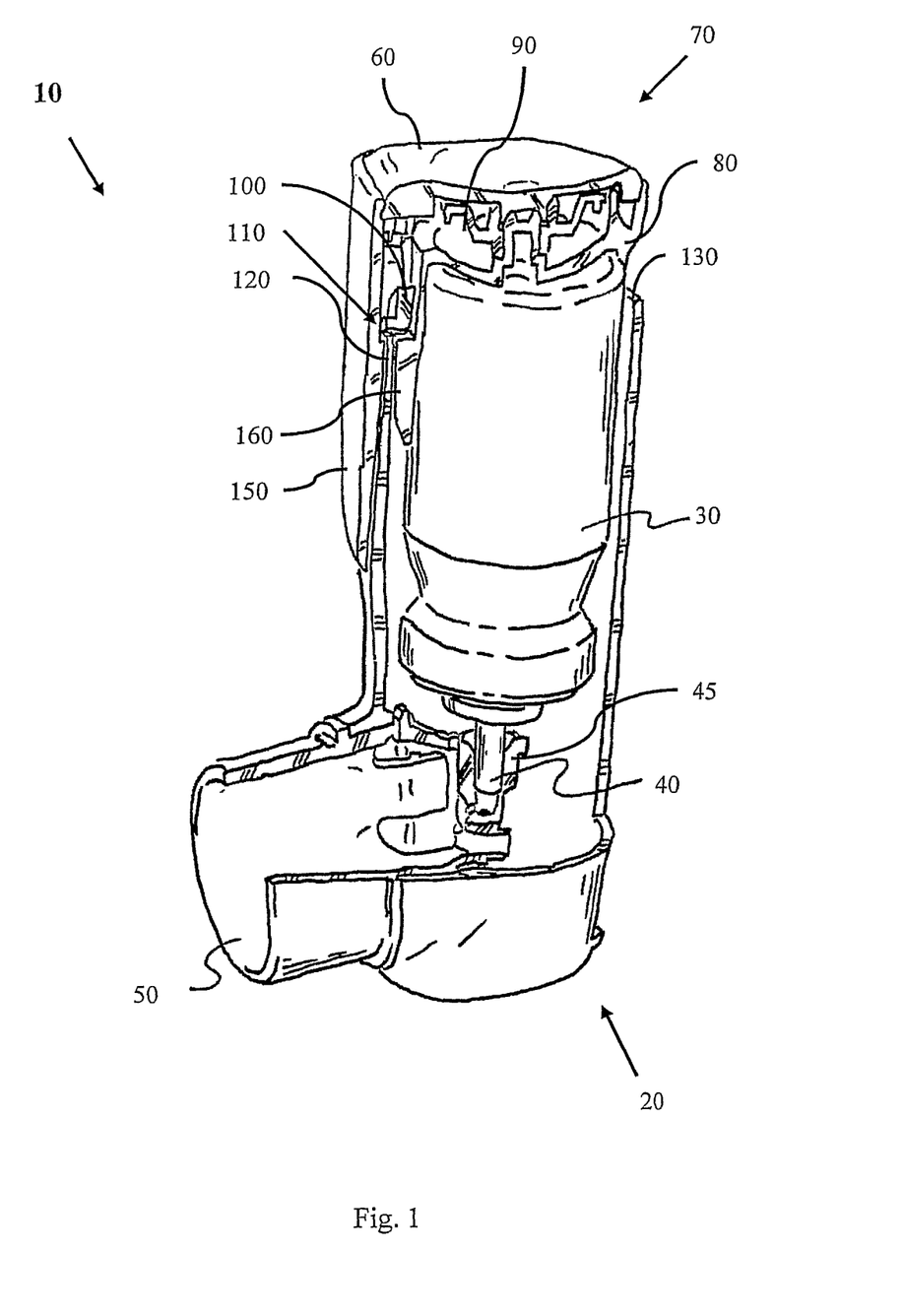
FIG. 1 shows a partially sectional perspective view of an embodiment of an inhaler device according to the present invention.

In FIG. 1 an inhalation device 10 according to one embodiment of the invention is shown. It comprises an actuator body 20, which encloses a canister 30 holding the medicament. The medicament is delivered to the user through a valve stem 40 connected to the top of the canister 30 (lower part of the canister in the figure due to the invert position of the canister in the inhalation device). The medicament is inhaled by the user through a mouthpiece 50 that is apart of the actuator body 20. The mouthpiece 50 is in connection with the valve stem 40 via a stem receiving body 45 for receiving the medicament to be delivered. Furthermore a dose counter unit 60 is provided at the base end of the canister 30, i.e. in the opposite end to the valve stem 40. In the embodiments disclosed herein, the dose counter unit 60 is preferably permanently attached to the canister 30, in order to avoid that the counter unit 60 is removed from one canister 30 and attached on another canister 30 containing a different level of medicament. The canister 30 with the attached dose counter unit 60 is hereafter referred to as an inhaler can assembly 70. When a dose of medicament should be delivered to the user, the inhaler can assembly 70 is pressed downwards whereby the valve stem 40 is forced into a position where it delivers a dose of medicament, or by other words is fired. This is in conformity with many inhalation devices according to the prior art and will not be described in more detail here.

The counting is related to the downward motion of the inhaler can assembly 70. The dose counter unit 60 should increase the number of counted doses by one every time a dose has been delivered. The dose counter unit 60 can either count up from zero or count down from a predetermined maximum number. Since undercounting is not to recommend due to the risk that the user believes that there is medicament left in the canister 30 when it actually is empty, the counter unit 60 usually is affected to count one count when the inhaler can assembly 70 has been pressed down a distance slightly less than is needed for delivering the dose of medicament.

The dose counter unit 60 comprises a counter housing 80 and a counter mechanism 90 with a counter actuator 100 for actuating the counter mechanism 90. The housing 80 is, in a downwards directed surface thereof, provided with an aperture 110 that is adapted to receive a protrusion 120 from the top edge 130 of the actuator body 20 in a mating relationship. Generally speaking, the aperture 110 and the protrusion 120 can be referred to as first and second position ensuring means respectively, as they ensure that the inhaler canister assembly 70 is received in the correct position with respect to the actuator body 20. In order to avoid that the inhaler device 10 is fired without the corresponding actuation of the dose counter unit 60, the top edge 130 of the actuator body including the protrusion 120, and the bottom surface 140 of the counter housing 80 are so formed that depression of the inhaler canister assembly 70 cannot be performed unless the protrusion 120 and the aperture 110 are positioned in the correct mating position. Moreover, when the inhaler can assembly 70 is depressed in order to fire the inhaler device 10, the protrusion 120 extends through the aperture 110 into the counter housing 80 and engages the counter actuator 100, and hence actuates the counter mechanism 90.

Figure 2A:
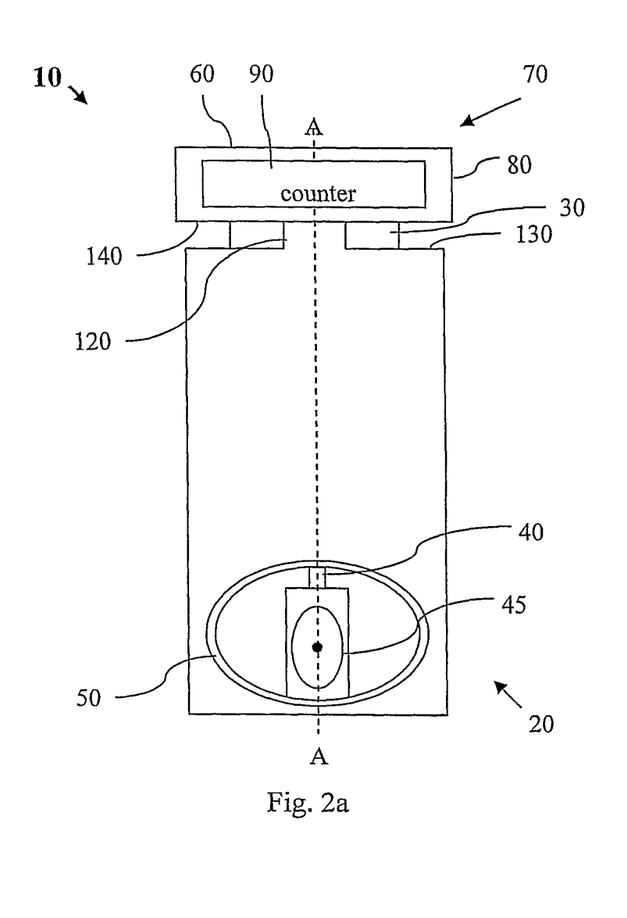
FIG. 2*a* shows a schematic front view of an inhaler device according to the present invention.
Figure 2B:
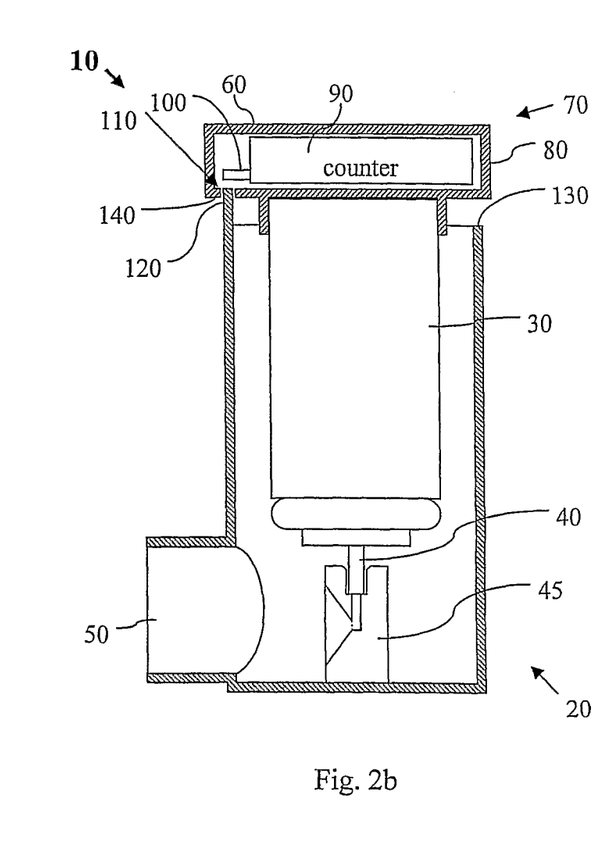
FIG. 2*b* shows a schematic cross-sectional view along the line a-a of the inhaler device in FIG. 2*a*.
Figure 3A:
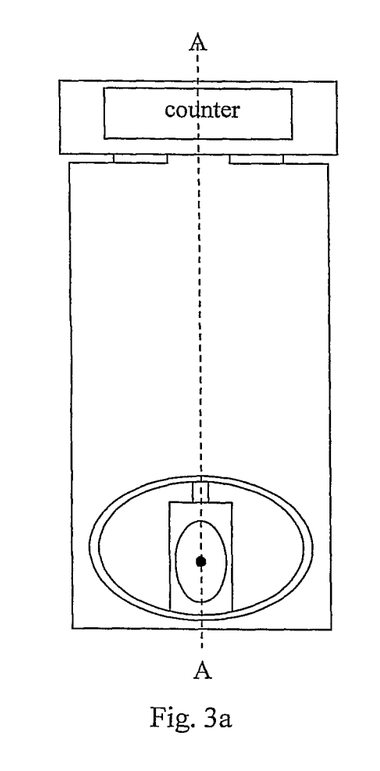
FIGS. 3*a* and 3*b*, show schematic views of the inhaler device of FIGS. 2*a* and 2*b* in a firing state.
Figure 3B:
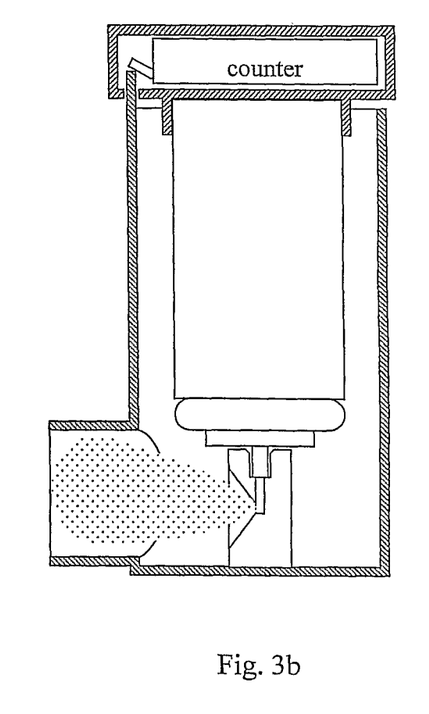
Figure 4A:
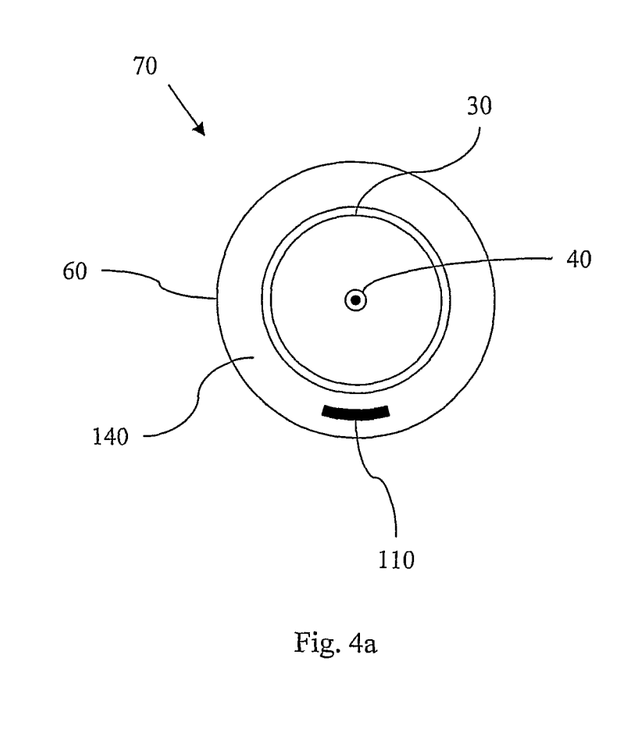
FIG. 4*a* shows a schematic top view of the inhaler can assembly of FIG. 2*a*.
Figure 4B:
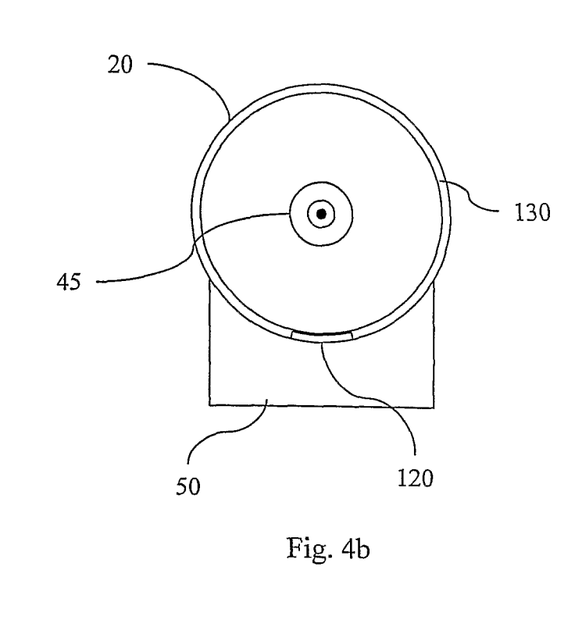
FIG. 4*b* shows a schematic bottom view of the actuator body of FIG. 2*b*.

FIGS. 2a, 2b, 3a, 3b, 4a and 4b more clearly show the relationship between the protrusion 120 and the aperture 110 in the counter housing 60 of the inhaler can assembly 70. As is shown in these figures, the inhaler device 10 has two states of operation: normal state and firing state. In the normal state that is shown in FIGS. 2a and 2b, the metering valve of the canister 30 is closed and the protrusion 120 is aligned with the aperture 110 but not affecting the counter actuator 100. In the shown example, the protrusion 120 extends a small distance into the aperture 110, but in other embodiments the protrusion 120 may be located completely outside the aperture 110, as long as the protrusion 120 must enter the aperture 110 in order for the inhaler device 10 to be fired and for actuating the dose counter unit 60. In the firing state that is shown in FIGS. 3a and 3b, the metering valve is depressed so that a metered dose of medicine is delivered to a user via the mouthpiece 50. In the firing state the protrusion 120 extends through the aperture 110 into the counter housing 80 and actuates the counter actuator.

As can be appreciated by FIGS. 2a and 2b, the inhaler canister assembly 70 must be placed in the correct position with respect to the actuator body 20 in order for the protrusion 120 to fit into the aperture 110. If the inhaler canister assembly 70 is placed in the wrong position, the protrusion 120 will abut against the bottom surface 140 of the counter housing 80, and the firing operation cannot be performed. Furthermore, as the protrusion 120 will not extend through the aperture 110 into the counter housing 80, the counter actuator 100 is not actuated.

In a general embodiment of the inhaler device 10 the inhaler canister assembly 70 comprises first position ensuring means 110, the actuator body 20 comprises second position ensuring means 120, wherein the first and second position ensuring means 110, 120 are complementary mating means, and the first and second position ensuring means 110, 120 are so arranged that the inhaler device 10 cannot be fired, nor the counter unit 60 be actuated unless the first and second position ensuring means 110, 120 are in a mating relationship. In the embodiments disclosed above, the protrusion 120 serves as the second position ensuring means, and it also serves to actuate the counter actuator 100 and thus the counter unit 60. However, the actuation of the counter actuator 100 might be performed by alternative means separated from the position ensuring means, as long as the counter actuator 100 cannot be actuated unless the first and second position ensuring means are in mating relationship.

Figure 5A:
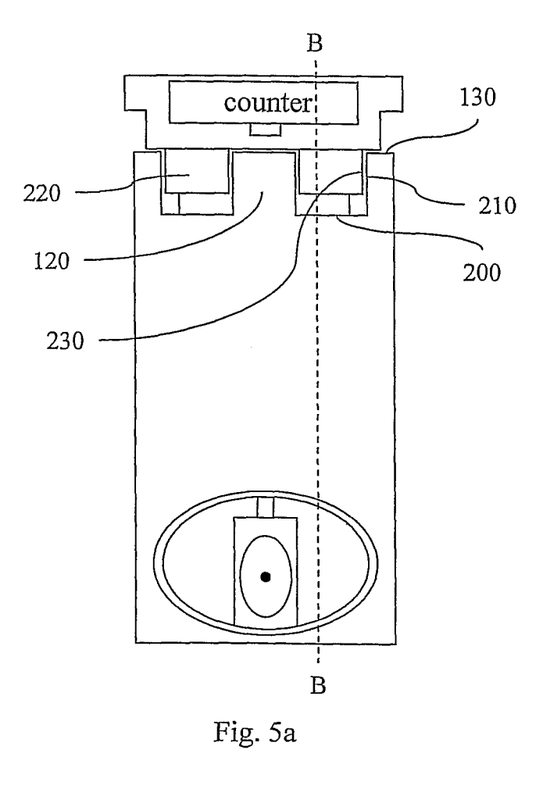
FIG. 5*a* shows a schematic front view of an embodiment of the inhaler device according to the present invention.
Figure 5B:
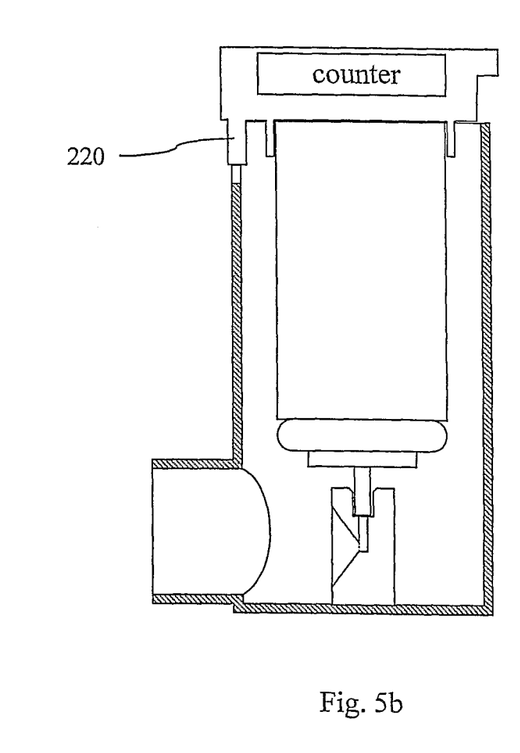
FIG. 5*b* shows a schematic cross-sectional view along the line b-b of the inhaler device in FIG. 5*a*.

It should be appreciated that there might be more than one pair of mating position ensuring means, which all cooperate to ensure that the inhaler canister assembly and the actuator body are positioned in a correct relationship, of which pairs at least one pair is comprised of a protrusion 120 from the actuator body 20 and a mating aperture 110 in the counter housing 80, and which protrusion 120 actuates the counter unit 60 in the firing operation. FIGS. 5a and 5b schematically shows an alternative embodiment of the inhaler device according to the present invention, wherein the protrusion 120 is provided at a lower level 200 than the main portion of the upper edge 130 of the actuator body 20. In this embodiment, the essentially vertical portions 210 of the upper edge 130 interacts with essentially vertical side portions 230 of the downwards extending sections 220 of the counter housing 80 in order to form a secondary pair of position ensuring means. In this embodiment the protrusion 120 is protected from accidental damage by the secondary pair of position ensuring means, as they e.g. prevents the protrusion 120 from excessive angular forces that can be applied by a user on the counter housing and potentially break the protrusion, if the secondary position ensuring means were not present. If the protrusion is damaged/removed, then the device could be fired and the counter would not count; therefore the device would under-count i.e. display that there were more doses remaining than there actually were, a dangerous situation.

By arranging the counter actuator 100 so that it is activated by the relatively small sized protrusion 120 that has to be inserted into a mating aperture 110, the risk for accidental actuation, as well as willful tampering is minimized, as it requires that a similar small sized object has to be introduced into the aperture 110.

In the disclosed embodiment, the protrusion 120 and the mating aperture 110 have a rectangular cross section, but it may be given any suitable shape. The protrusion 120 may further be formed such that the aperture 110 or first position ensuring means takes the form of a grove or a slit in the counter housing 80. In one embodiment, the shape of the protrusion/aperture 110, 120 is used to identify e.g. the content or concentration contained in the canister 30 and actuator bodies 20 adapted for delivering specific medicines, respectively, in order to avoid that a inhaler canister assembly 70 is used with an improper actuator body 20.

In the disclosed embodiments, the actuation of the inhaler device 10 is performed by a linear relative movement of the inhaler canister assembly 70 with respect to the actuator body 20. However, the actuation could also be an angular relative movement, or a combination thereof, and the first and second position ensuring means thus being adapted to the path of the movement.

Figure 6:
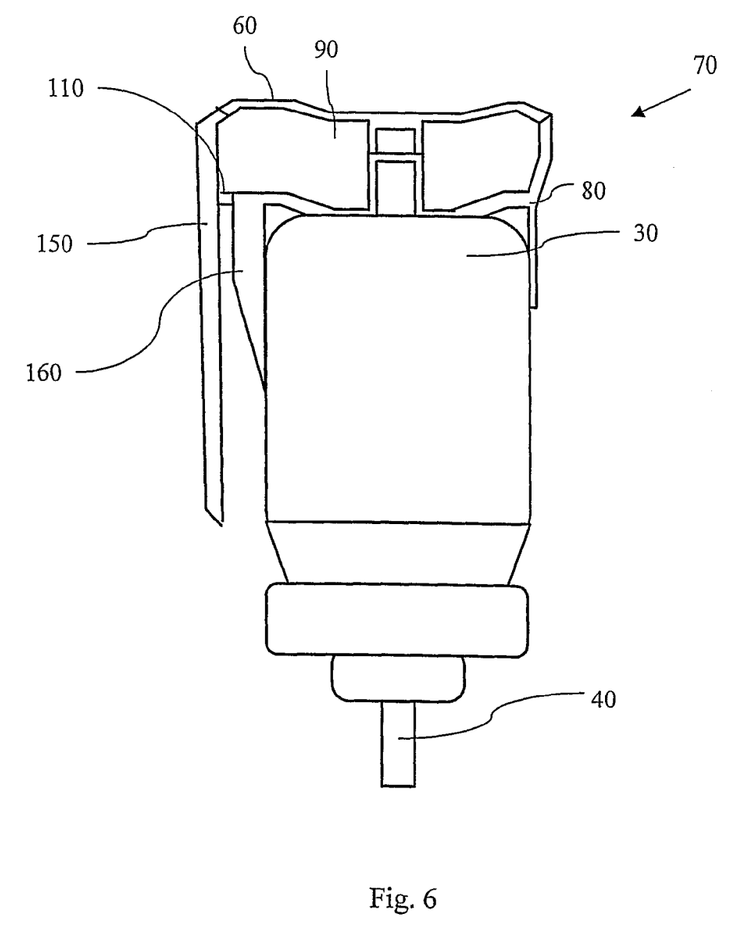
FIG. 6 shows a schematic cross-sectional view of the counter unit of FIG. 1.

FIG. 6 shows a schematic cross sectional view of the inhaler canister assembly 70 of the inhaler device 10 in FIG. 1, and the following description refers to both figures. For clarity reasons the parts of the counter mechanism are omitted in FIG. 4. The dose counter unit 60 comprises a protecting shield 150 that extends downwards from the counter unit 60 adjacent to the outer surface of the actuator body 20. The protecting shield 150 further ensures that that dose counter unit 60 cannot be actuated by mistake, as it is positioned adjacent to the aperture 110 and thus further obstructs access to the aperture 110. Moreover, during the firing operation, the shield 150 covers the protrusion 120 and the aperture 110 and thus protects them from being obstructed in their relative movement. The inner surface of the protecting shield 150 further serves as a guide means for guiding the protrusion 120 into mating relationship with the aperture 110. Alternatively, the inner surface of the protecting shield 150 can be provided with guide means in the form of ridges or the like. The dose counter unit 60 further comprises guiding means between the aperture and the outer surface of the canister 30 in the form of an inclined surface or ridge 160. Furthermore, the protecting shield provides a large surface which allows a clear label to be added to the front of the device (dose level, drug etc) because the counter is attached in the normal position for the drug label (around the base of the canister).

The invention claimed is:

1. An inhaler device, comprising:
an actuator body and an inhaler canister assembly, the actuator body having a proximally located opening configured to receive part of the inhaler canister assembly, the inhaler canister assembly is comprised of a canister with a distally located metering valve and a proximally located dose counter unit,
wherein the inhaler canister assembly comprises a proximally located first position-ensuring member, the actuator body comprises a proximally located second position-ensuring member,
wherein at least one of the first and second position-ensuring members includes a protrusion and the other of the first and second position-ensuring members includes an aperture configured to receive part of the protrusion to form a complementary mating system, and the first and second position-ensuring members being so arranged that the inhaler device cannot be fired, nor the dose counter unit count unless the first and second position-ensuring members are in a mating relationship whereby the protrusion is aligned with the aperture during a normal state and the protrusion extends through the aperture to actuate the counter unit during a firing state.

2. The inhaler device according to claim 1, wherein the inhaler device is fired by a relative motion of the inhaler canister assembly with respect to the actuator body, and the first and second position-ensuring members being arranged to prevent said relative motion of the inhaler canister assembly, when they are positioned in a non mating relationship whereby the protrusion does not align with the aperture.

3. The inhaler device according to claim 1, wherein the aperture includes at least one of a mating aperture, a groove, and a slit in the inhaler canister assembly.

4. The inhaler device according to claim 1, wherein the first position-ensuring member is formed in the dose counter unit.

5. The inhaler device according to claim 4, wherein the second position-ensuring member is arranged to act as an actuator for the dose counter unit.

6. The inhaler device according to claim 4, wherein, when the canister assembly is placed in the actuator body, the first and second position-ensuring members are covered by a protecting shield that extends downwards from the dose counter unit adjacent to an outer surface of the actuator body.

7. The inhaler device according to claim 4, further including a guiding system for guiding the second position-ensuring member into mating relationship with the first position-ensuring member.

8. The inhaler device according to claim 7, wherein the guiding system is provided on an inner side of a protecting shield.

9. The inhaler device according to claim 7, wherein the guiding system is provided between the first position-ensuring member and an outer surface of the canister.

10. The inhaler device of claim 1, wherein the first position-ensuring member and the second position-ensuring member are located adjacent to a proximal end of the canister.

11. The inhaler device of claim 1, wherein the canister is attached to the dose counter unit.

12. The inhaler device of claim 1, wherein the aperture is formed in a bottom surface of the inhaler canister assembly and the protrusion extends from a top edge of the actuator body.

13. The inhaler device of claim 12, wherein the bottom surface is substantially planar.

14. The inhaler device of claim 1, wherein the first position-ensuring member includes a bottom surface of the dose counter unit.

15. The inhaler device of claim 1, wherein the dose counter unit is located proximal to the canister.

16. The inhaler device of claim 1, wherein the protrusion at least partially resides within the aperture during the normal state.

17. The inhaler device of claim 1, further including a third position-ensuring member having a second protrusion and a fourth position-ensuring member having a second aperture configured to receive part of the second protrusion, the third and fourth position-ensuring member being so arranged that the inhaler device cannot be fired, nor the counter unit count unless the second protrusion at least partially resides within the second aperture.

18. The inhaler device of claim 1, wherein the canister includes a medicament.

19. An inhaler canister assembly comprising:
a canister with a distally located metering valve and a proximally located dose counter unit, the inhaler canister assembly forming an inhaler device when combined with an actuator body having an opening configured to receive at least part of the canister; and
a proximally located first position-ensuring member that is configured to complementary mate with a second position-ensuring member of the actuator body,
wherein the first position-ensuring member includes at least one of a protrusion and an aperture that is configured to complementary mate with a respective aperture or protrusion of the second position-ensuring member, and the first position-ensuring member being so arranged that the inhaler device cannot be fired, nor the dose counter unit count unless the first position-ensuring member is in a mating relationship with the second position-ensuring member, whereby the protrusion is configured to align with the aperture during a normal state and the protrusion is configured to extend through the aperture to actuate the counter unit during a firing state.

20. The inhaler canister of claim 19, wherein the canister includes a medicament.

21. An actuator body forming an inhaler device when combined with an inhaler canister assembly, the inhaler canister assembly is comprised of a canister with a metering valve located at a distal end, and a dose counter unit located at a proximal end thereof, the actuator body comprising:
a proximally located opening configured to receive part of the inhaler canister assembly and a proximally located second position-ensuring member that is configured to complementary mate with a first position-ensuring member of the inhaler canister assembly,
wherein the second position-ensuring member includes at least one of a protrusion and an aperture that is configured to complementary mate with a respective aperture or protrusion of the first position-ensuring member, and the second position-ensuring member being so arranged that the inhaler device cannot be fired, nor the dose counter unit count unless the second position-ensuring member is in a mating relationship with the first position-ensuring member, whereby the protrusion is configured to align with the aperture during a normal state and the protrusion is configured to extend through the aperture to actuate the counter unit during a firing state.

22. The inhaler canister of claim 21, wherein the canister includes a medicament.

23. An inhaler device comprising:
an inhaler canister assembly comprising a canister and a dose counter unit, the canister comprising a metering valve, the dose counter unit comprising a counting actuator, the inhaler canister assembly including two apertures with at least one aperture providing access to the counting actuator;
an actuator body receiving the canister, the actuator body comprising two protrusions, the two protrusions being complementary to the two apertures such that, when the two protrusions are aligned with the two apertures, the actuator body can be moved relative to the inhaler canister assembly to actuate the metering valve and to pass at least one of the two protrusions through the at least one aperture to actuate the dose counter mechanism, wherein the two protrusions, when not aligned with the two apertures, prevent the relative movement of the actuator body and the inhaler canister assembly in a direction that would actuate the metering valve.

24. The inhaler device of claim 23, wherein the two protrusions, when not aligned with the two apertures, prevent the relative movement of the actuator body and the inhaler canister assembly in a direction that would actuate the metering valve by abutting a surface of the inhaler canister assembly.

25. The inhaler device of claim 23, wherein at least one of the two apertures is a slit.

26. The inhaler device of claim 23, wherein the dose counter unit comprises a counter housing containing the counting actuator, wherein the counter housing defines the at least one aperture providing access to the counting actuator.

27. The inhaler device of claim 26, wherein the two protrusions, when not aligned with the two apertures, prevent the relative movement of the actuator body and the inhaler canister assembly in a direction that would actuate the metering valve by abutting a surface of the counter housing.

28. The inhaler device of claim 23, wherein the inhaler canister assembly further comprises a protecting shield that extends from the dose counter unit adjacent the actuator body.

29. The inhaler device of claim 28, wherein the protecting shield covers the two protrusions and the two apertures to protect against obstruction of their relative movement and to obstruct external access to the two apertures.

30. The inhaler device of claim 28, wherein the protecting shield comprises a ridge to guide the two protrusions into the two apertures.

31. The inhaler device of claim 23, wherein the canister includes a medicament.

* * * * *